United States Patent [19]

Lehman

[11] Patent Number: 5,337,739
[45] Date of Patent: Aug. 16, 1994

[54] DISPOSABLE BACTERIA FILTER

[75] Inventor: Arlin D. Lehman, Louisville, Colo.

[73] Assignee: Polmonary Data Service Instrumentation, Inc., Louisville, Colo.

[21] Appl. No.: 929,817

[22] Filed: Aug. 14, 1992

[51] Int. Cl.$^5$ ............................ A62B 7/10; A61B 5/08
[52] U.S. Cl. .................... 128/205.27; 128/719
[58] Field of Search ............... 128/719, 720, 725, 728, 128/204.23, 205.12, 205.27, 205.29, 206.17, 206.12, 202.28; 73/861.52; 55/486, 279, 267, 492

[56] References Cited

U.S. PATENT DOCUMENTS

| | | | |
|---|---|---|---|
| 4,181,512 | 1/1980 | Kippel et al. | 128/205.29 |
| 4,360,018 | 11/1982 | Choksi | 128/205.29 |
| 4,640,293 | 2/1987 | Gorbe | 128/725 |
| 4,707,167 | 11/1987 | Saito et al. | 55/279 |
| 5,005,568 | 4/1991 | Loescher et al. | 128/202.28 |
| 5,230,727 | 7/1993 | Pound et al. | 55/492 |

*Primary Examiner*—William E. Kamm
*Assistant Examiner*—Brian M. Greer
*Attorney, Agent, or Firm*—Rick Martin

[57] ABSTRACT

An interchangeable set of wide orifice respiratory filter elements can be built into either a low resistance, high dead space embodiment for forced vital capacity testing or high resistance, low dead space embodiment for diffusion and residual air tests. A disposable 3M Filtrete ™ pad is at the heart of all embodiments thus allowing extremely high levels of filtration efficiencies.

15 Claims, 7 Drawing Sheets

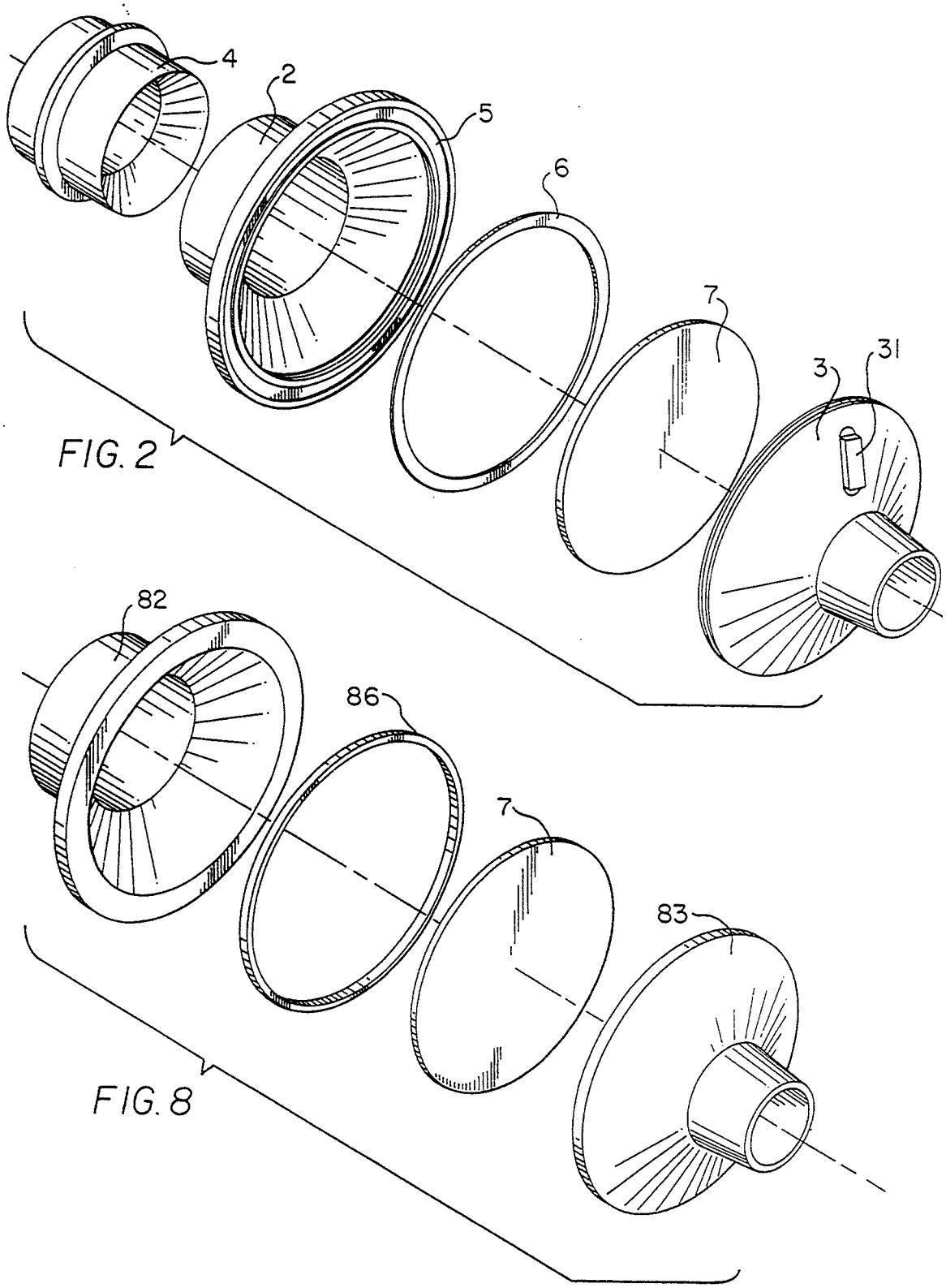

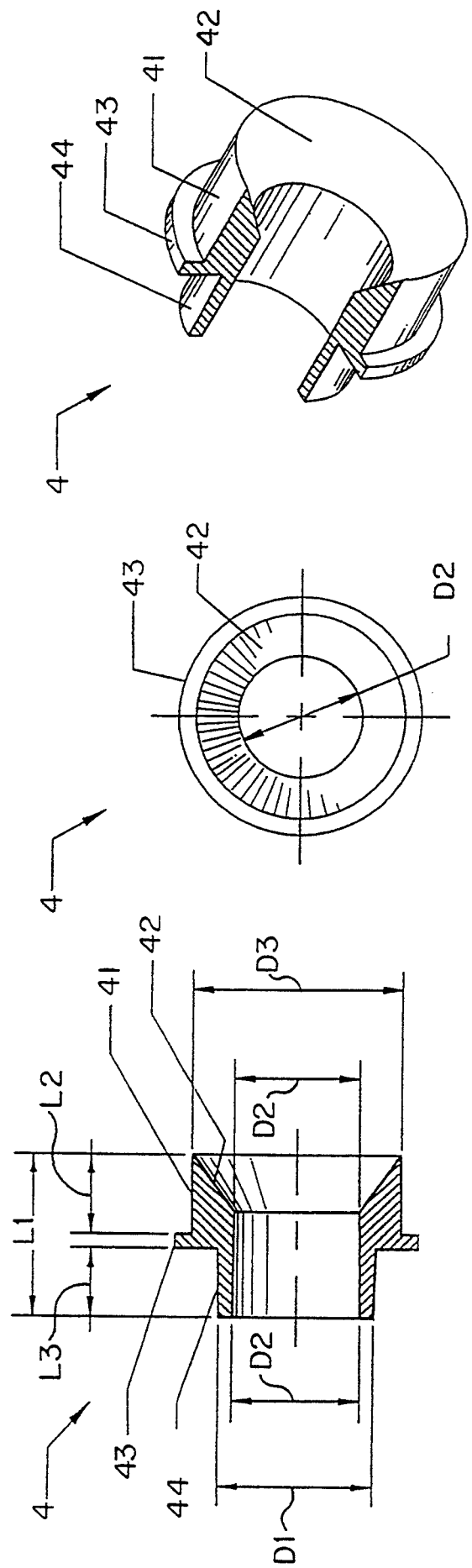

DISPOSABLE BACTERIA FILTER

FIELD OF THE INVENTION

The present invention relates to disposable bacteria filters especially suitable for spirometers, ventilators and related respiratory apparatus.

BACKGROUND OF THE INVENTION

Spirometry is the art of determining the health and capacity of the lungs. Original instruments comprised a mouthpiece, blowtube, water cylinder, ballast and chart recorder. The patient blew into the mouthpiece, thereby lifting the ballast a measurable height for a measurable time. Time versus displacement graphs could be combined with the patient's age, weight and medical history to help diagnose lung diseases.

In the past few years the use of computers for spirometry measurement has become commonplace. As a consequence the American Thoracic Society (ATS) publishes and updates a Standardization of Spirometry for spirometry systems including the disposable mouthpiece.

Modern health care facilities perform countless spirometry tests annually. Spirometers can be the cause of spreading bacteria and viruses resulting in the spread of serious diseases including TB and HIV. Cleansing reusable mouthpieces and instrument parts is a costly and risky procedure. This is especially true considering the control procedures necessary for monitoring compliance of numerous test personnel working under time pressure.

The result of the undesirability of cleansing reusable mouthpieces and instrument parts has led to the development of several disposable mouthpiece designs. Before discussing the development of disposable mouthpieces we must first review some testing basics.

There are three basic tests performed by spirometers. They are first a forced vital capacity test, second a diffusion test, and third a lung volume test. Spirometers used in the office of a physician generally perform only the vital capacity test while the instruments used by a hospital or pulmonary physician are usually capable of performing all three tests. These instruments which perform all three tests are sometimes called total lung analyzers, but they are actually spirometers.

The forced vital capacity test simply measures time versus flow. Low filter resistance is required to assure accurate flow readings. The diffusion test measures the efficiency of oxygen transfer from the alveoli to the blood. This test uses minute amounts of carbon monoxide breathed into the lungs through a closed loop spirometry system. This test requires low dead space in the filter apparatus to assure accurate readings of minute amounts of carbon monoxide. Finally the lung volume test uses a small amount of helium in a closed loop system to measure the lungs' residual air after expiration. This test also requires a leak proof seal in the filter apparatus to prevent leakage of helium.

Thus these three tests require different characteristics from the filter apparatus. These ideal characteristics are:
1) Low resistance
2) High filtration efficiency of bacteria
3) Low dead space
4) Leak proof seal Further economic and environmental characteristics of the ideal filter are:
5) Low cost
6) Universal mounting capabilites on dozens of spirometers
7) Reduced volumetric disposal of plastics It should be noted that low resistance is most easily obtained by having a large dead space and a wide area for gas flow through the filter. Also a minimal filtration efficiency offers a low resistance.

Two main disposable filter systems comprise the prior art. First the Pall Barrier Filter TM uses a baffle type barrier which is 99.9% effective in filtering particulate matter including spit. But the barrier is noneffective on airborn bacteria on the order of 0.2 microns. The Pall filter has a very low resistance around 0.4 cm $H_2O$/liter/second at 12 liters per second flow. The ATS standard for the total spirometry instrument is less than 1.5 cm $H_2O$/liter/second at 12 liters per second flow. The internal dead space of the Pall filter is very low at 40 cc. The cost is quite high at $5 per unit. In summary the Pall filter fails to block airborn bacteria (ATS specs do not specify a standard) and is expensive.

The second known disposable filter is the Marquest TM filter. It uses a 3M ® gauze filter named Filtrete ® at a thickness of 200 gm/sq.m. It is 99.99% efficient in filtering airborn bacteria and 99.98% efficient for viruses. Thus, the Marquest filter efficiently filters bacteria and viruses. However, in order to obtain a resistance of about 0.9 cm $H_2O$/filter/second at 12 liters per second flow, Marquest creates a large 3½" diameter orifice thus a large surface area for the Filtrete ®, thereby creating about 150 cc's of dead space. ATS calls for 150 cc's of dead space for the total spirometer. Thus, the Marquest filter is not suitable for either the diffusion test or the lung volume test. The price, however, at $3.50 is quite an advantage over the Pall filter.

Another embodiment of the Filtrete ® filter uses too thin a gauge of Filtrete ® spread across a 2" diameter orifice. This approach creates an acceptably low dead space but an unacceptably high resistance. The filtration efficiency is also dramatically reduced. The cost is very low at $1.00 each. Thus, this embodiment does not satisfy the market demands.

The present invention uses interchangeable housing components in combination with 3½" diameter Filtrete ® discs to meet all seven market demands:
1) low resistance at 0.9 cm $H_2O$/liter/second at 12 liters per second flow.
2) 99.99% and 99.98% efficient in stopping airborn bacteria and viruses respectively.
3) Low dead space ranging from 90 to 115 cc's.
4) Leak proof design.
5) Low cost at $1.65 each.
6) Universal mounting adapters.
7) Only the mouthpiece is disposed, thus cutting the waste plastic in half, or for a reusable mouthpiece embodiment, only the filter pad is disposed.

SUMMARY OF THE INVENTION

The primary object of the present invention is to provide a highly efficient disposable bacteria/virus filter having low resistance to air flow.

Another object of the present invention is to provide this filter with an option to sacrifice low resistance for low dead space for certain tests.

Another object of the present invention is to provide this filter with a universal mounting adapter.

Another object of the present invention is to provide this filter with optional reusable or throw away mouthpieces.

Another object of the present invention is to provide this filter with a leak proof fast assembly design.

A final object of the present invention is to provide this filter with a low cost basis.

Other objects of this invention will appear from the following description and appended claims, reference being had to the accompanying drawings forming a part of this specification wherein like reference characters designate corresponding parts in the several views.

BRIEF DESCRIPTION OF THE DRAWINGS

FIG. 2 is a top perspective view of a disassembled disposable filter.

FIG. 3(a) is a longitudinal cross sectional view of the adapter 4 shown in FIG. 2.

FIG. 3(b) is a front plan view of the adapter 4 shown in FIG. 2.

FIG. 3(c) is a top perspective view having a partial cutaway of the adapter 4 shown in FIG. 2.

FIG. 8 is a top perspective view of a disassembled disposable filter having a push together design.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DETAILED DESCRIPTION OF THE PREFERRED EMBODIMENT

Figure 1:
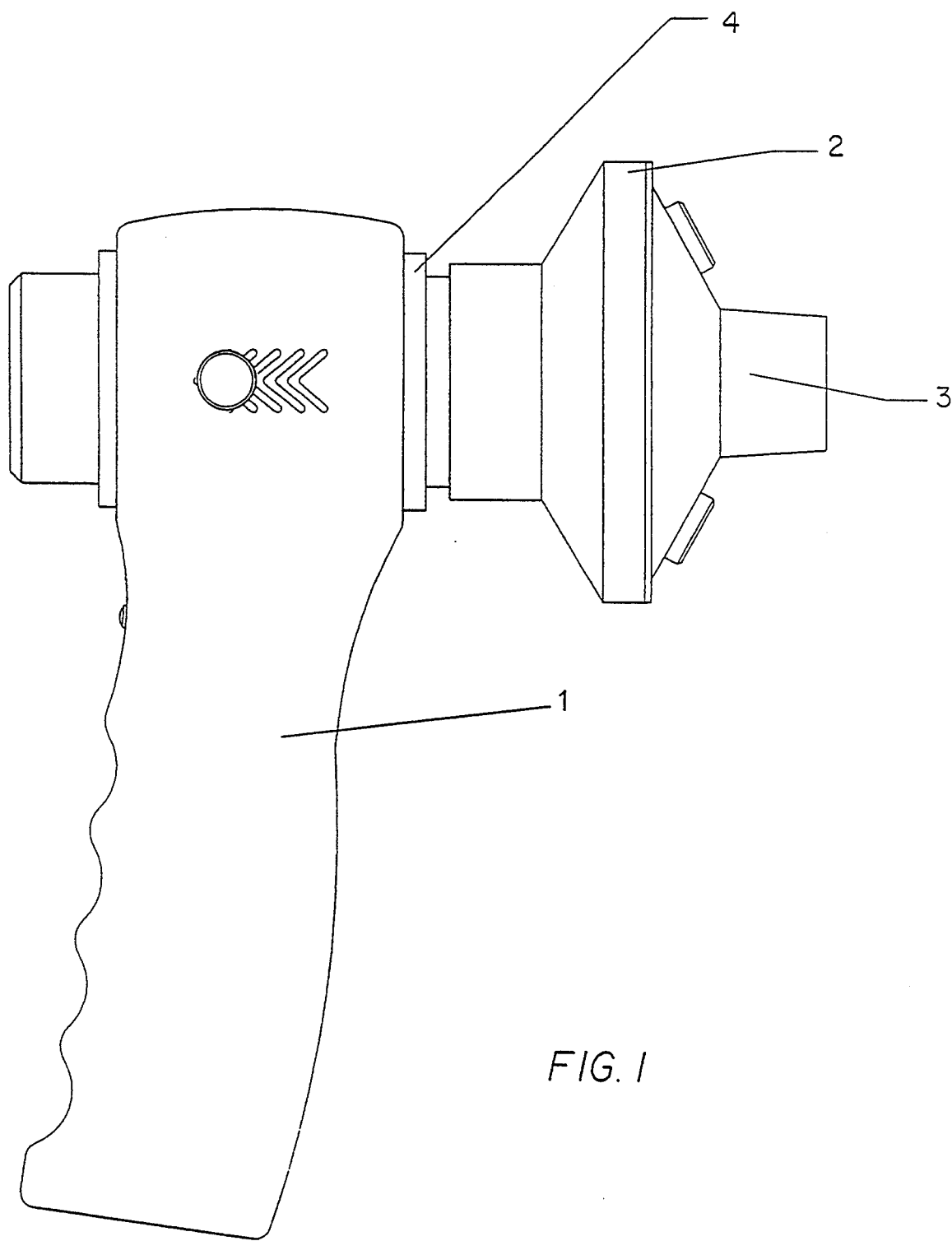
FIG. 1 is a top perspective view of a spirometer having a detachable disposable filter.

FIG. 1 shows a spirometer 1 which senses a patient's respiratory parameters and sends these parameters to a computer (not shown) for diagnostic analysis. The patient breathes into mouthpiece 3. FIG. 2 shows a filter pad 7 housed inside the mouthpiece 3. This filter pad must prevent over 99% of airborn bacteria and viruses from passing through it. The best known material for filter pad 7 is a fibrous pad made by 3M and named Filtrete ® which has tested at 99.99% efficient in filtering airborn bacteria having diameters as low as 0.2 microns and 99.98% efficient in filtering airborn viruses having diameters as low as 0.02 microns. A proper thickness to achieve these efficiencies over a 3½" blow tube orifice is 200 gm/sq.m.

Figure 6C:
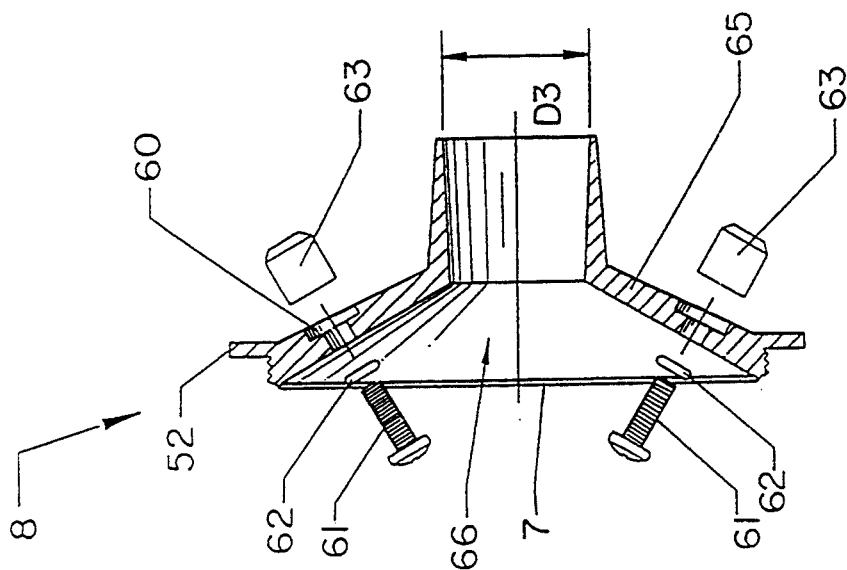
FIG. 6(c) is a longitudinal cross section of the reusable mouthpiece shown in FIGS. 6(a)(b).
Figure 6B:
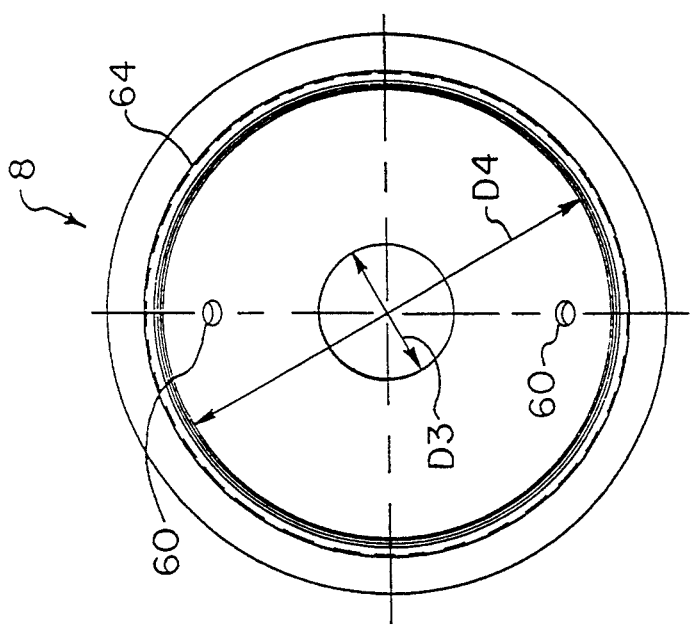
FIG. 6(b) is a front plan view of the reusable mouthpiece 8 shown in FIG. 6(a).
Figure 6A:
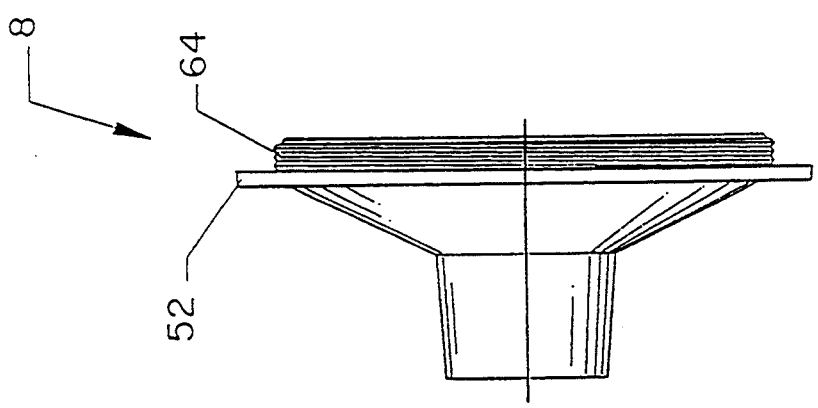
FIG. 6(a) is a side plan view of a reusable mouthpiece.

Mouthpiece 3 has a tightening ridge 31 which is used to securely screw mouthpiece 31 into housing 2. Mouthpiece 3 is a light gauge throw away type. FIGS. 6(a)(b)(c) and 7(a)(b)(c) show a heavier duty reusable mouthpiece which uses a hole 60, tightening nut 63, washer 62, and bolt 61 design to provide a leak proof rugged tightening means.

In FIG. 2 is shown a filter pad 7 held in a leakproof manner between mouthpiece 3 and housing 2. O ring 6 fitted into groove 5 ensures a leakproof fit between housing 2 and mouthpiece 3. Adapter 4 provides the connection between spirometer 1 and housing 2.

Referring next to FIG. 3 adapter 4 has a divider 43, housing mate 41, housing mate flang 42, and a spirometer mate 44. Inside diameter D2 is constant throughout the adapter 4. The dimensions D1, D3, L1, L2, L3, are all different for various embodiments of adapter 4, providing a means for mounting housing 2 on any spirometer. Adapter 4 may be made of a hard plastic or a soft plastic or rubber. Adapter 4 is not disposable. It remains affixed to the spirometer 1 even when changing from unfilled housing 2 in FIGS. 1, 2, 4(a)(b) to filled housing 20 in FIGS. 5(a)(b).

The resistance of the filter assemblies 4, 2, 6, 7, (3 or 8) is approximately 0.9 cm $H_2O$/liter/second at 12 liters per second flow. This is well below the ATS standard of 1.5 cm $H_2O$/liter/second at 12 liters per second flow for the overall spirometer system.

Figure 4C:
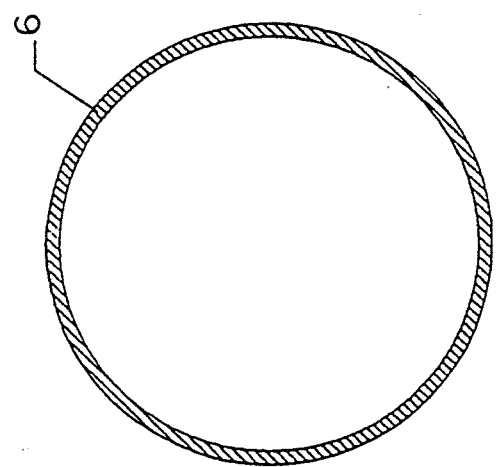
FIG. 4(c) is a front plan view of the O ring 6 shown in FIG. 2.
Figure 4B:
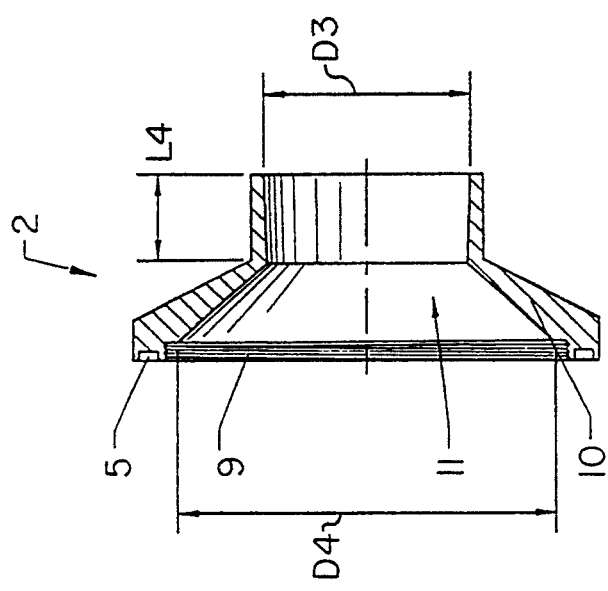
FIG. 4(b) is a longitudinal cross sectional view of the housing 5 shown in FIG. 2.

For diffusion and lung volume testing normal tidal breathing is used with low flow rates where filter resistance is very small. Therefore, filled housing 20 in FIGS. 5(a)(b) in combination with filled reusable mouthpiece 80 in FIGS. 7(a)(b)(c) create very low dead spaces 111 and 660. The total dead space of filter assembly 4, 20, and 80 is approximately 90 cc's. This is reduced from an approximate 150 cc's of dead space for the low resistance filter assembly 4, 2, 8 shown in FIGS. 2, 4, 6.

Figure 4A:
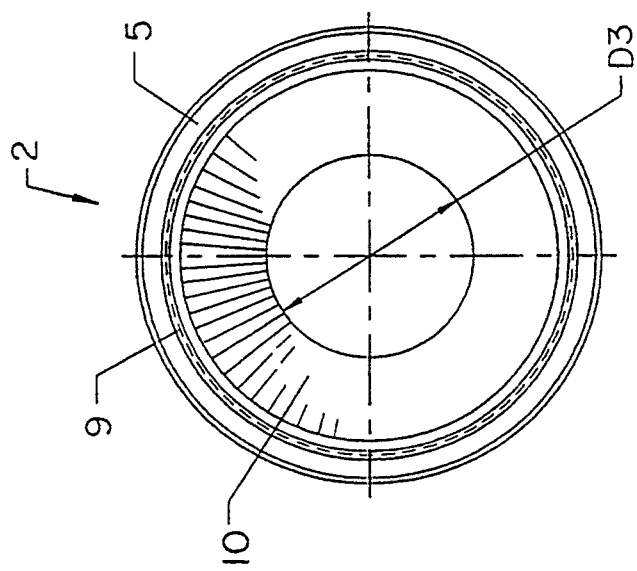
FIG. 4(a) is a front plan view of the housing 5 shown in FIG. 2.

In FIGS. 4(a)(b)(c) D3 is about 1½", D4 is about 3½", and L4 is about ¾". Housing flang 10 ends with female threads 9 and grove 5. O ring 6 fits into groove 5 so as to tightly seat against sealing lip 52 on mouthpiece 8 in FIG. 6(a). Dead space 11 is maximized to allow low resistance when high pressure is blown through mouthpiece 8.

Figure 5B:
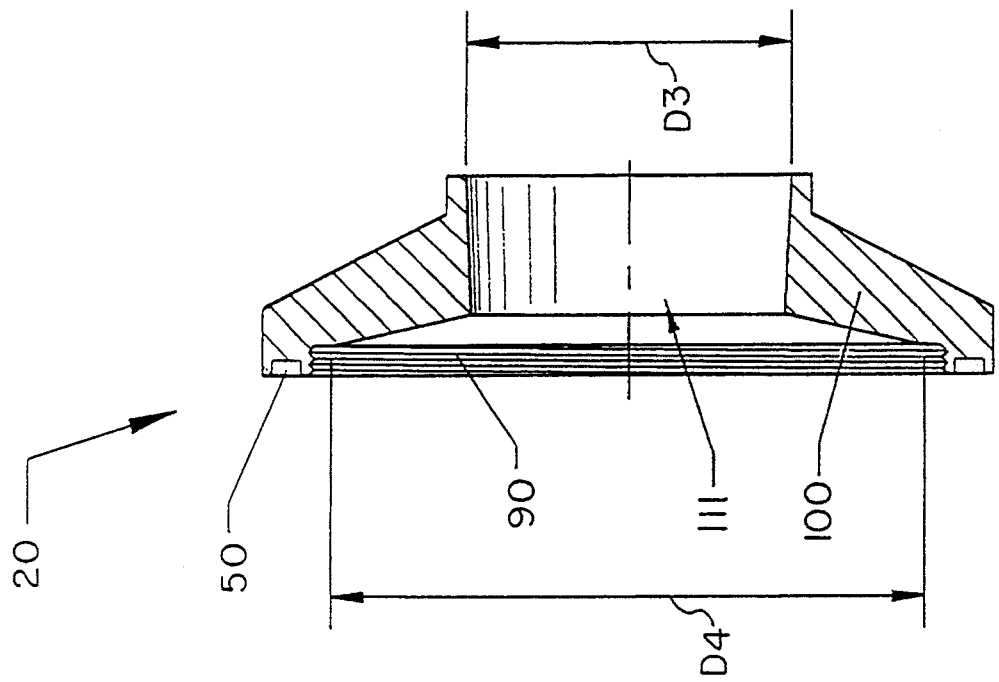
FIG. 5(b) is a longitudinal cross section of the filled housing 20 shown in FIG. 5(a).
Figure 5A:
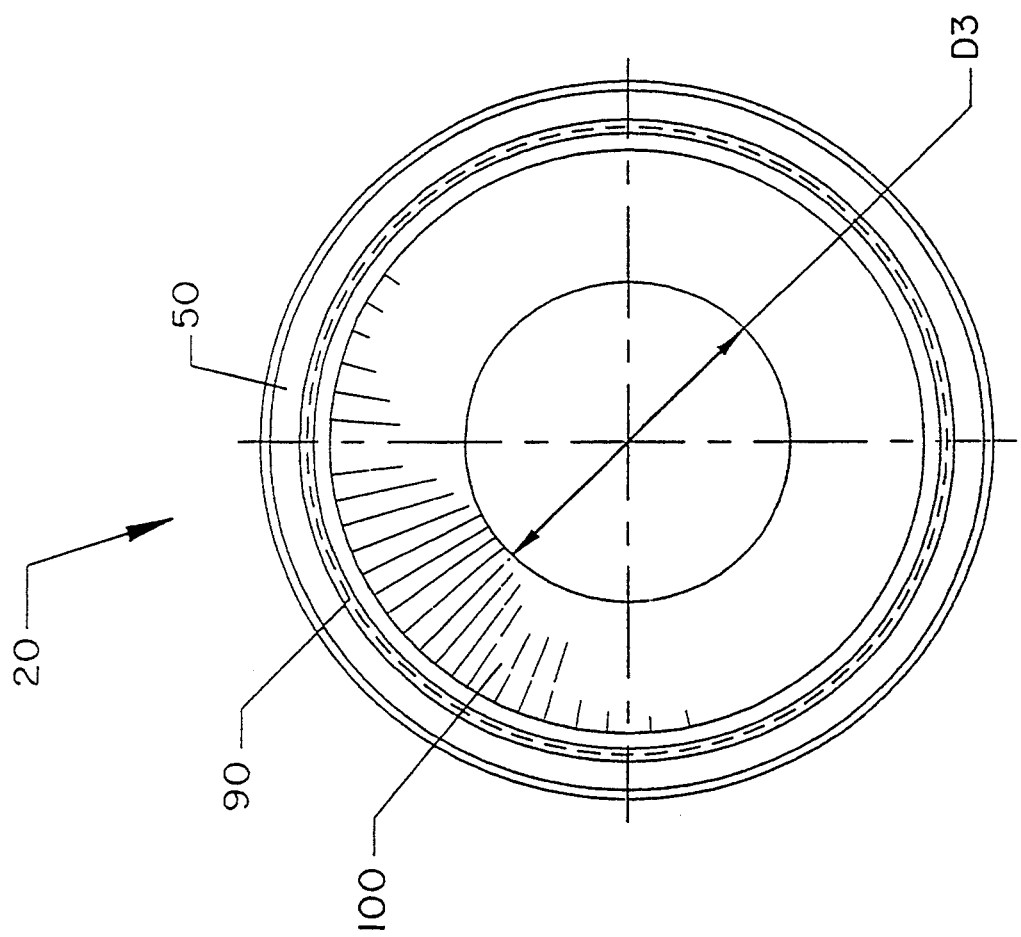
FIG. 5(a) is a front plan view of a filled housing.

In FIG. 5 is shown filled housing 20. D3 and D4 remain the same. However, dead space 111 has been minimized by filled housing flang 100. Groove 50 is the same as groove 5 and uses O ring 6. Female threads 90 are the same as female threads 9. Thus, filled housing 20 is interchangeable with unfilled housing 2. And filled reusable mouthpiece 8 or unfilled throw away mouthpiece 3.

In FIGS. 6(a)(b)(c) sealing lip 52 seals O ring 6 in FIG. 4. Male threads 64 mate with female threads 9 of FIGS. 4(a)(b). Dead space 66 is maximized to reduce flow resistance.

Figure 7C:
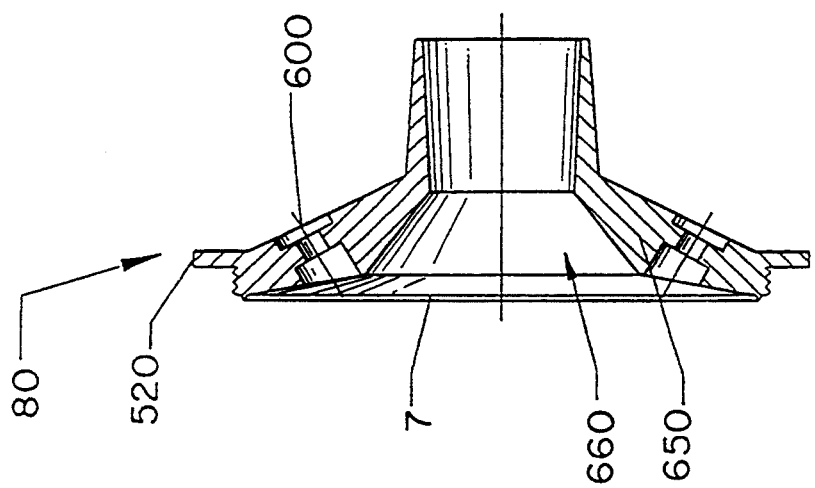
FIG. 7(c) is a longitudinal cross section of the filled housing 80 shown in FIGS. 7(a)(b).
Figure 7B:
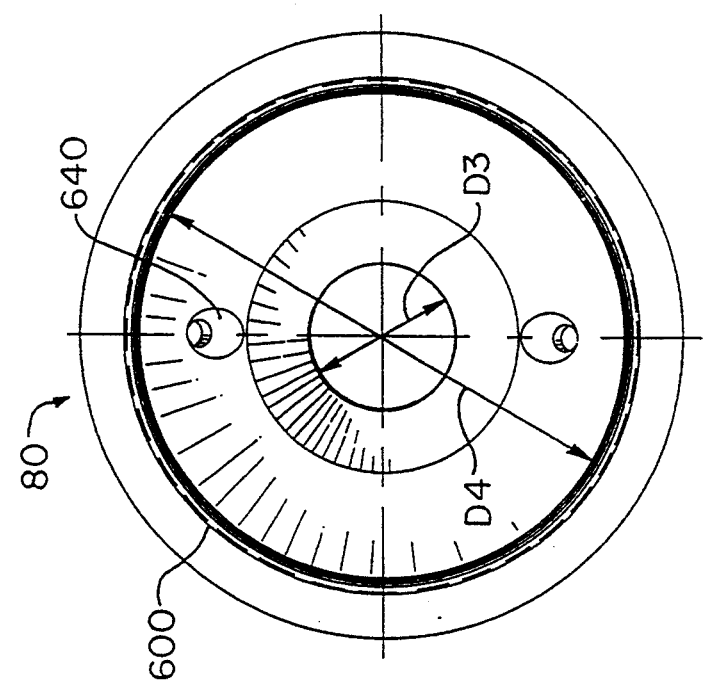
FIG. 7(b) is a front plan view of the filled housing 80 shown in FIG. 7(a).
Figure 7A:
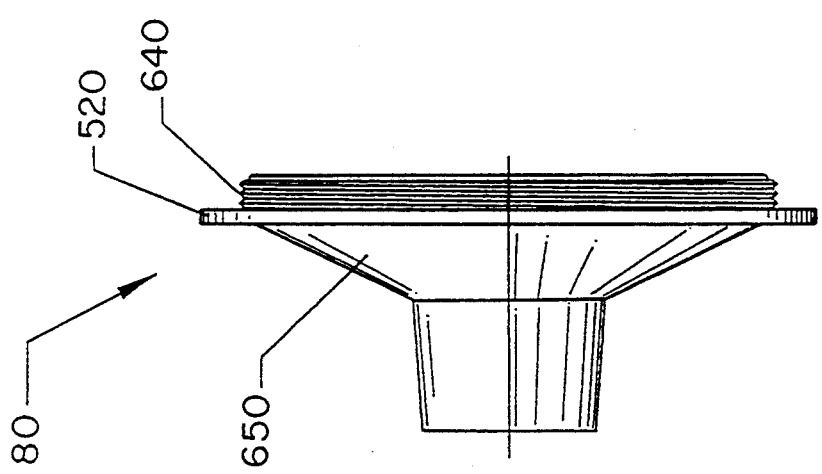
FIG. 7(a) is a side plan view of a filled housing.

In FIG. 7(a)(b)(c) is shown interchangeable reusable mouthpiece 80 having reduced dead space 660 and filled mouthpiece flang 650.

ATS standards call for a total dead space for the diffusion and residual air tests of the spirometer and filter combination of under 150 cc's.

The adapter 4 plus the filled housing 20 plus the filled mouthpiece 80 have a total dead space of 90 cc's.

Another embodiment of the invention is disclosed in FIG. 8. Using housing 82 without threads nor a groove, mouthpiece 83 is placed snuggly into housing 82 with filter 7 in between. With housing 82 snuggly connected to mouthpiece 83 a rubberband 86 is placed around the perimeter of housing 82 and mouthpiece 83 to create the necessary leakproof seal between housing 82 and mouthpiece 83.

Dynamic testing was performed on the present invention using filter assembly 2, 3, 4 by injecting each of the 24 standard wave forms recommended by the American Thoracic Society Standardization of spirometry. (Am Rev Respir Dis 1987; 136:1285-1298) using a computer driven spirometry simulator. Each wave form was injected at least once. If, for any wave form, the results did not meet the ATS recommendations, that wave form was injected several more times to determine if the observed error was consistent. The target values used were slightly different from those published by the American Thoracic Society. The spirometry simulator and computer algorithm have been improved; the target values used represented the best estimate of the actual flow delivered by the simulator.

ATS standards required the forced vital capacity (FVC) and time forced expiratory volume (FEVt) be within 3.5% or 70 ml of target, whichever is larger. For mean forced expiratory flow during the middle half of the FVC, FEF25-75%, the requirement is that the measured value be within 5.5% or 0.25 liters/second, whichever is larger.

The present invention with a conventional spirometer measured all three parameters on all 24 wave forms without error.

I claim:

1. A respiratory filter comprising:
   a housing;
   a removable mouthpiece;
   a means for a leakproof coupling between said housing and said removable mouthpiece;
   means for filtration mounted between said housing and said removable mouthpiece; and
   said means for filtration further comprising an airflow resistance of 0.9 cm $H_2O$/liter/second or less at 12 liters per second flow.

2. The respiratory filter of claim 1, further comprising an adapter having a divider separating an instrument mate and a respiratory filter housing mate.

3. The respiratory filter of claim 1, wherein said housing further comprises a housing flang, a dead space, and said housing flang further comprising said means for a leakproof coupling to said removable mouthpiece.

4. The respiratory filter of claim 3, wherein said means for a leak proof coupling further comprises female threads in said hosing flange, a groove, and an O-ring compressibly mounted in said groove, and said removable mouthpiece further comprises male threads coacting with said female threads.

5. The respiratory filter of claim 3, wherein said housing flang is filled, thereby reducing said housing dead space to approximately 45 cc's and increasing said airflow resistance.

6. The respiratory filter of claim 4, wherein said removable mouthpiece further comprises a mouthpiece flang substantially similar to said housing flang, a mouthpiece dead space and said mouthpiece flang further comprising a sealing lip, and matching said male threads to said female threads, wherein screwing said male threads into said female threads compresses said O ring between said sealing lip and said groove, thereby forming said means for a leakproof coupling between said housing and said removable mouthpiece.

7. The respiratory filter of claim 6, wherein said mouthpiece flang is filled, thereby reducing said mouthpiece dead space to approximately 45 cc's and increasing said airflow resistance.

8. The respiratory filter of claim 1, wherein said removable mouthpiece is reusable and further comprises means for tightening.

9. The respiratory filter of claim 8, wherein said means for tightening further comprises protruding finger bolts.

10. The respiratory filter of claim 1, wherein said means for filtration further comprises a disposable pad of fibrous matter capable of filtering 99.99% of airborn bacteria and 99.98% of airborn viruses.

11. The respiratory filter of claim 10, wherein said disposable pad further comprises Filtrete ® at a density of 200 gm/sq.m over a 3.5" orifice.

12. A respiratory filter apparatus comprising:
   a reusable housing;
   a mouthpiece;
   a disposable filter pad mounted between said housing and said mouthpiece;
   means for coupling and sealing said reusable housing and said mouthpiece in a leakproof manner, wherein said assembly comprising said reusable housing, said mouthpiece, and said disposable filter pad further comprises an airflow resistance of approximately 0.9 cm $H_2O$/liter/second or less at 12 liters per second flow;
   an interchangeable second filled reusable housing;
   an interchangeable second filled mouthpiece, wherein said assembly comprising said interchangeable second filled reusable housing, said interchangeable second filled mouthpiece, and said disposable filter pad further comprises a total dead space of approximately 90 cc's.

13. An improvement on the disposable filter apparatus on a spirometer; the improvement comprising:
   a housing;
   a mouthpiece;
   a disposable filter pad mounted between said housing and said mouthpiece;
   means for coupling and sealing said housing and said mouthpiece in a leakproof manner, wherein said assembly comprising said housing, said mouthpiece, and said disposable filter pad and said spirometer further comprises an airflow resistance of less than 1.5 cm $H_2O$/liter/second at 12 liters per second flow;
   an interchangeable second filled housing;
   an interchangeable second filled mouthpiece, wherein said assembly comprising, said interchangeable second filled housing, said interchangeable second filled mouthpiece, and said disposable filter and said spirometer further comprises a total dead space less than 150 cc's.

14. The respiratory filter of claim 13, wherein said means for coupling and sealing said housing and said mouthpiece in a leakproof manner, further comprises a push tight fitting between said housing and said mouthpiece and a leakproof flexible member surrounding said push tight fitting.

15. The respiratory filter of claim 14, wherein said leakproof flexible member further comprises a rubberband.

* * * * *